(12) United States Patent
Southern et al.

(10) Patent No.: US 11,518,765 B2
(45) Date of Patent: *Dec. 6, 2022

(54) SUBSTITUTED PYRIMIDINE DERIVATIVES USEFUL IN THE TREATMENT OF AUTOIMMUNE DISEASES

(71) Applicant: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE)

(72) Inventors: John Michael Southern, Dublin (IE); Stephen J. Connon, Dublin (IE)

(73) Assignee: THE PROVOST, THE FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 17/004,097

(22) Filed: Aug. 27, 2020

(65) Prior Publication Data
US 2021/0024529 A1   Jan. 28, 2021

Related U.S. Application Data

(62) Division of application No. 15/514,739, filed as application No. PCT/EP2015/072486 on Sep. 29, 2015, now Pat. No. 10,793,572.

(51) Int. Cl.
*A61P 37/00* (2006.01)
*A61K 31/519* (2006.01)
*C07D 487/04* (2006.01)
*A61P 37/02* (2006.01)

(52) U.S. Cl.
CPC .......... *C07D 487/04* (2013.01); *A61K 31/519* (2013.01); *A61P 37/02* (2018.01)

(58) Field of Classification Search
CPC ............... A61P 37/00; A61K 31/519
See application file for complete search history.

(56) References Cited

U.S. PATENT DOCUMENTS

| | | |
|---|---|---|
| 4,435,569 A | 3/1984 | Mishimura |
| 4,571,423 A | 2/1986 | Nomura |
| 5,002,950 A | 3/1991 | Malone et al. |
| 5,061,707 A | 10/1991 | Kostlan |
| 5,312,900 A | 5/1994 | Armstrong |
| 6,106,864 A | 8/2000 | Dolan et al. |
| 6,596,701 B1 | 7/2003 | Schwartz et al. |
| 2003/0078231 A1 | 4/2003 | Wilburn |
| 2009/0286782 A1 | 11/2009 | Ibrahim |
| 2011/0256130 A1 | 10/2011 | Schultz |

FOREIGN PATENT DOCUMENTS

| | | |
|---|---|---|
| EP | 0079447 A1 | 5/1983 |
| EP | 0089055 A2 | 9/1983 |
| EP | 0119591 A1 | 9/1984 |
| EP | 0260491 A1 | 3/1988 |
| JP | S5936615 A | 2/1984 |
| JP | S6056980 A | 4/1985 |
| WO | 8803142 | 5/1988 |
| WO | 98/55148 A | 12/1988 |
| WO | 91/11172 A | 8/1991 |
| WO | 94/02518 A | 2/1994 |
| WO | 00/35295 A1 | 6/2000 |
| WO | 2009/082247 A1 | 7/2009 |
| WO | 2012/150866 A1 | 11/2012 |

OTHER PUBLICATIONS

English Translation of Japanese Office Action for Application No. 2017-516829, dated Jun. 18, 2019, 8 pages.
Maralidhar et al., "Identifying inhibitors of queuine modification of tRNA in cultured cells," Science Direct, Analytical Biochemistry 171(2):346-351 (1988).
Palace et al., "New Treatments and Azathioprine in Multiple Sclerosis," The Lancet 350(9073): 261 (1997).
U.S. Appl. No. 15/514,968, Office Action dated Jan. 10, 2018.
U.S. Appl. No. 15/514,968, Office Action dated Mar. 14, 2018.

(Continued)

*Primary Examiner* — Bruck Kifle
(74) *Attorney, Agent, or Firm* — Hoffman Warnick LLC (57) ABSTRACT

The present invention describes compounds of formula (I)

(I)

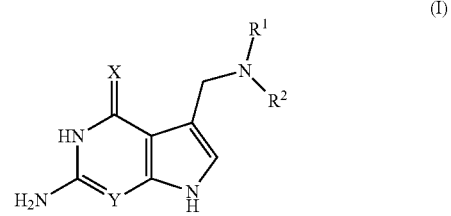

Wherein:
$R^1$ is selected from H and $CH_3$
$R^2$ is selected from H, $C_4H_9$ alkyl, $C_6H_{13}$ alkyl and $C_3H_6$-phenyl, said phenyl optionally substituted by OH or $OCH_3$, (1R,2S,5S)-5-methylcyclopent-3-ene-1,2-diol
X is O or S
Y is C, N or S.

These compounds have been identified as novel compounds useful in the treatment of multiple sclerosis and other autoimmune diseases.

16 Claims, 3 Drawing Sheets

(56) References Cited

OTHER PUBLICATIONS

U.S. Appl. No. 15/514,968, Election of Species Requirement dated Sep. 26, 2017.
Stromnes et al., "Active Induction of Experimental Allergic Encephalomyelitis," Nature Protocols 1(4):1810-1819 (2006).
Brooks, "Synthesis of Tritium Labeled Queuine, PreQ1 and Related Azide Probes Toward Examining the Prevalence of Queuine," Dissertation at the University of Michigan, 202 pages (2012).
Olgen et al., "Synthesis and Activity of Novel 5-Subsitute Pyrrolo[2,3-d]pyrimidine Analogues as pp60c-Src Tyrosine Kinase Inhibitors," Arch. Pharm. Chem. Life Sci. 341:113-120 (2008).
Liang et al., "Fast-dissolving intraoral drug delivery systems," Expert Opinion on Therapeutic Patents 11(6):981-986 (2001).
Akimoto et al., "Synthesis of Queuine, the Base of Naturally Occurring Hypermodified Nucleoside (Queuosine), and its Analogues," J. Chem. Soc. Perkin Trans. I, 1637-1644 (1988).
Akimoto et al., "Queuine Analogues. Their Synthesis and Inhibition of Growth Mouse L5178Y Cells in Vitro," J. Med. Chem. 29:1749-1753 (1986).
Boland et al., "Queuosine formation in eukaryotic tRNA occurs via mitochondrial localized heteromeric transglycosylase," J. Biol. Chem. (2009).
Polman et al., "Drug Treatment of Multiple Sclerosis," BMJ 321:490-494 (2000).
Brooks et al., "A short, concise synthesis of queuine," Tetrahedron Letters 51:4163-4165 (2010).
Verma et al., "Current Status of Drug Delivery Technologies and Future Directions," Pharmaceutical Technology 25(2):1-14 (2001).
PCT Patent Application Serial No. PCT/EP2015/072486 International Search Report dated Nov. 11, 2015, 3 pages.
GB Patent Application Serial No. GB 1417163.1 Combined Search and Examination Report dated Jul. 20, 20-15, 2 pages.
Hoops et al., "Mechanism-Based inactivation of tRNA-Guanine Transglycosylase from *Escherichia coli* by 2-Amino-5-(fluoromethyl)pyrrolo[2,3-d]pyrimidin-4(3H)-one," Biochemistry 34(47):15539-15544 (1995).

Varhese "The Queuine-Transfer RNA Pathway as a novel drug mechanism to treat Multiple Sclerosis," WorldCat Thesis/dissertation XP002749107, available at www.worldcat.org/title/queuine-transfer-ma-pathway-as-a-novel-drug-mechanism-to-treat-multiple-sclerosis/ocic/856580202 (2015).
Pathak et al., "Queuine promotes antioxidant defence system by activating cellular antioxidant enzyme activities in cancer," Bioscience Reports 28(2):73-81 (2008).
Okada et al., "Novel mechanism of post-transcriptional modification of tRNA insertion of bases of Q precursors into tRNA by a specific tRNA transglycosylase reaction," The Journal of Biological Chemistry 254(8):3067-3073 (1979).
Shindo-Okada et al., "Transfer ribonucleic acid guanine transglycosylase isolated from rat liver," Biochemistry 19(2):395-400 (1980).
Gerber et al., "Concise and efficient synthese of preQ1 base, Q base and (ent)-Q base," Organic & Biomolecular Chemistry 10(43):8660-8668 (2012).
Kverka et al., "Safety and efficacy of the immunosuppressive agent 6-tioguanine in murine model of acute and chronic colitis," MBC Gastroenterology 11(1):47-55 (2011).
Mason et al., "Thioguanine for refractory psoriasis: A 4-year experience," Journal of American Academy of Dermatology 44(1):67-72 (2001).
Shindo-Okada et al., "Queuine analogues. Their synthesis and inhibition of growth of mouse L5178Y cells in vitro," J. Med. Chem. 29(9):1749-1753 (1986).
PCT Patent Application Serial No. PCT/EP2015/072488 International Search Report dated Jan. 27, 2016, 3 pages.
GB Patent Application Serial No. 1417165.6 Combined Search and Examination Report dated Aug. 10, 2015, 2 pages.
PCT Patent Application Serial No. PCT/EP2015/072488 International Preliminary Report on Patentability dated Apr. 4, 2017, 8 pages.
PCT Patent Application Serial No. PCT/EP2015/072486 International Preliminary Report on Patentability dated Apr. 4, 2017, 8 pages.

SUBSTITUTED PYRIMIDINE DERIVATIVES USEFUL IN THE TREATMENT OF AUTOIMMUNE DISEASES

CROSS-REFERENCE TO RELATED APPLICATIONS

This is a divisional application of co-pending U.S. patent application Ser. No. 15/514,739, filed 27 Mar. 2017, which is the US national phase of then-co-pending PCT Patent Application Serial No. PCT/EP2015/072486, filed 29 Sep. 2015, which in turn claims priority to GB Patent Application Serial No. 1417163.1, filed 29 Sep. 2014, each of which is hereby incorporated herein.

TECHNICAL FIELD

The invention relates to novel substituted pyrimidine derivatives useful in the treatment of autoimmune diseases, particularly multiple sclerosis. This invention also relates to the use of such compounds in the treatment of autoimmune diseases, particularly multiple sclerosis and to pharmaceutical compositions containing such compounds.

BACKGROUND ART

Multiple sclerosis (MS) is a debilitating disease of the central nervous system (CNS) in which the body's own immune system attacks the white matter of the brain and spinal cord. This triggers inflammation-induced damage to the CNS protective myelin layer causing demyelination. Loss of myelin exposes neurons to further attack leading to formation of multiple sclerotic lesions. This damage disrupts the ability of parts of the nervous system to communicate, resulting in a wide range of problems including fatigue, blurred vision, cognitive impairment, and spasticity.

Many patients suffer from the development of irreversible motor disability. Long term prognosis is poor, within 15 years of disease onset approximately 50% of patients are unable to walk unassisted (Polman and Uitdehaag, B. M. J., 2000, 321, 490-494).

MS takes several forms, with new symptoms either occurring in isolated attacks (relapsing forms) or building up over time (progressive forms).

There is at present no known cure for multiple sclerosis. Current treatments attempt to improve function after an attack and/or prevent subsequent attacks. Medications used to treat MS, while modestly effective, can have adverse effects and be poorly tolerated.

There are a number of injectable front line therapies:
- beta interferon 1a (Avonex)
- beta interferon 1a (Rebif)
- beta interferon 1b (Betaferon)
- glatiramer acetate (Copaxone)

Interferons may produce flu-like symptoms and some people taking glatiramer experience a post-injection reaction with flushing, chest tightness, heart palpitations, breathlessness, and anxiety, which usually lasts less than thirty minutes. More dangerous but much less common is liver damage. Copaxone is associated with skin irritation at the site of injection Additional therapies include:
- Natalizumab reduces the relapse rate more than first-line agents; however, due to issues of adverse effects such as progressive multifocal leukoencephalopathy it is a second-line agent reserved for those who do not respond to other treatments or with severe disease.
- Fingolimod (Gilenya)—licensed in March 2011 for people with rapidly evolving severe relapsing remitting MS (two or more relapses a year), and as a second line treatment for people whose MS remains active despite treatment with one of the beta interferon drugs.
- Dimethyl fumarate (Tecfidera) was licensed by the FDA in 2013 and is an oral first line therapy for adults with relapsing remitting forms of MS.
- Teriflunomide (Aubagio) was approved by the FDA in September 2012, is an orally available immunomodulatory drug for the treatment of relapsing forms of MS
- Mitoxantrone, whose use is limited by severe adverse effects, systolic dysfunction, infertility, and acute myeloid leukemia is a third-line option for those who do not respond to other medications.

Corticosteroids (or steroids) are sometimes given for a few days, either in the form of tablets or by intravenous drip. While there is no evidence that steroids have any effect on the long-term course of the disease, they can be effective at speeding up recovery from relapse.

No treatment has been shown to change the course of primary progressive MS and as of 2011 only one medication, mitoxantrone, has been approved for secondary progressive MS. In this population, tentative evidence supports mitoxantrone moderately slowing the progression of the disease and decreasing rates of relapse over two years.

There is ongoing research looking for more effective, convenient, and tolerable treatments for relapsing-remitting MS.

Monoclonal antibodies have raised high levels of interest. The CD52 monoclonal antibody alemtuzumab, CD25 monoclonal antibody daclizumab and CD20 monoclonal antibodies such as rituximab, ocrelizumab and ofatumumab have all shown some benefit and are under study as potential treatments. Their use has also been accompanied by the appearance of potentially dangerous adverse effects, most importantly opportunistic infections.

Accordingly, there is a huge unmet medical need for the treatment of MS.

SUMMARY OF THE INVENTION

In one aspect, the invention provides a method of treating an autoimmune disease in a mammal, the method comprising: administering to said mammal an amount of 2-amino-5-((((1S,4S,5R)-4,5-dihydroxycyclopent-2-en-1-yl)amino)methyl)-3,7-dihydro-4H-pyrrolo[2,3-d]pyrimidin-4-one or a pharmaceutically acceptable salt thereof sufficient to treat said autoimmune disease.

In another aspect, the invention provides a pharmaceutical composition comprising: 2-amino-5-((((1S,4S,5R)-4,5-dihydroxycyclopent-2-en-1-yl)amino)methyl)-3,7-dihydro-4H-pyrrolo[2,3-d]pyrimidin-4-one or a pharmaceutically acceptable salt thereof in an amount effective to treat an autoimmune disorder; and a pharmaceutically acceptable carrier or diluent.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

DETAILED DESCRIPTION

The present invention provides new medicaments for the treatment of autoimmune conditions, particularly multiple sclerosis. One embodiment of the invention describes compounds of formula (I)

(I)

and pharmaceutically acceptable salts and solvates thereof wherein:

$R^1$ is selected from H and $CH_3$ $R^2$ is selected from H, $C_4H_9$ alkyl, $C_6H_{13}$ alkyl and $C_3H_6$-phenyl, said Phenyl optionally substituted by OH or $OCH_3$, X is O or S Y is C, N or S.

Preferably alkyl chains are straight chain.

In a preferred embodiment, $R^1$ is H

In a preferred embodiment $R^2$ is selected from $C_4H_9$ alkyl, $C_6H_{13}$ alkyl and $C_3H_6$-phenyl.

In a particularly preferred embodiment $R^2$ is $C_3H_6$-phenyl

In a preferred embodiment X is O

In a preferred embodiment Y is C or N

In a particularly preferred embodiment Y is N

Particularly preferred are those compounds of formula (I) where:

X is O

Y is N $R^1$ is H; and $R^2$ is selected from $C_4H_9$ alkyl, $C_6H_{13}$ alkyl and $C_3H_6$-phenyl.

In a particularly preferred embodiment $R^2$ is $C_3H_6$-phenyl

Particularly preferred compounds of the invention include:

2-amino-5-((butylamino)methyl)-3,7-dihydro-4H-pyrrolo[2,3-d]pyrimidin-4-one

N-((2-amino-4-oxo-4,7-dihydro-3H-pyrrolo[2,3-d]pyrimidin-5-yl)methyl)butan-1-aminium chloride 2-amino-5-((hexylamino)methyl)-3,7-dihydro-4H-pyrrolo[2,3-d]pyrimidin-4-one N-((2-amino-4-oxo-4,7-dihydro-3H-pyrrolo[2,3-d]pyrimidin-5-yl)methyl)hexan-1-aminium chloride Queuine; 2-amino-5-((((1S,4S,5R)-4,5-dihydroxycyclopent-2-en-1-yl)amino)methyl)-3,7-dihydro-4H-pyrrolo[2,3-d]pyrimidin-4-one Queuine HCl 2-Amino-5-[[[(1S,4S,5R)-4,5-dihydroxy-2-cyclopenten-1-yl]amino]methyl]-1,7-dihydro-4H-pyrrolo[2,3-d]pyrimidin-4-one, monohydrochloride Most preferred is/are: 2-amino-5-(((3-phenylpropyl)amino)methyl)-3,7-dihydro-4H-pyrrolo[2,3-d]pyrimidin-4-one N-((2-amino-4-oxo-4,7-dihydro-3H-pyrrolo[2,3-d]pyrimidin-5-yl)methyl)-3-phenylpropan-1-aminium chloride;

Suitable salts include salts of acidic or basic groups present in compounds of formula (I). The compounds of formula (I) that are basic in nature are capable of forming a wide variety of salts with various inorganic and organic acids. The acids that may be used to prepare pharmaceutically acceptable acid addition salts of such basic compounds of formula 1 are those that form non-toxic acid addition salts. Suitable salts include acetate, benzenesulfonate, benzoate, bicarbonate, bisulfate, bitartrate, borate, bromide, calcium edentate, camsylate, carbonate, chloride, clavulanate, citrate, dihydrochloride edentate, edisylate, estolate, esylate, ethylsuccinate, fumarate, gluceptate, gluconate, glutamate, glycollylarsanilate, hexylresorcinate, hydrabamine, hydrobromide, hydrochloride, iodide isothionate, lactate, lactobionate, laurate, malate, maleate, mandelate, mesylate, methylsulfate, mucate, napsylate, nitrate, oleate, oxalate, pamoate, palmitate, pantothenate, phosphate, diphosphate, polygalacturonate, salicylate, stearate, subacetate, succinate, tannate, tartrate, teoclate, tosylate and valerate salts.

Preferred salts include hydrochloride and aminium chloride.

The subject invention also includes isotopically-labelled compounds which are identical to those described, but for the substitution of an atom for a corresponding isotope. Examples of isotopes include isotopes of hydrogen such as deuterium and tritium; isotopes of carbon such as $^{13}C$. Other examples are well known to those skilled in the art.

Where appropriate, compounds of the present invention include any cis/trans isomers.

The compounds of the present invention may be synthesised by a number of synthetic routes. Scheme 1 describes a conventional synthetic protocol for the synthesis of compounds of formula (I) where X & Y are as described herein.

Scheme 1

(I)

Compounds of formula (III) may be prepared from compounds of formula (II) by process step (i) addition of a suitable amine protecting group. The term 'PG' is used to denote any suitable protecting group. Suitable groups and conditions may be found in 'Protective Groups in Organic Synthesis' by Theodora W. Greene, Peter G. M. Wuts, 4th Edition, 2006, ISBN: 978-0-471-69754-1 published by Wiley Particularly favoured protecting groups are octyl alkyl amides, which result in lower levels of by-products and isomers in subsequent steps. Compounds of formula (IV) may be produced from compounds of formula (III) via process step (ii) which an electrophilic aromatic substitution reaction occurs between compound (iii) and the iminium ion formed by the condensation of dibenzylamine with formaldehyde under the standard conditions of the Mannich-type reaction. Compounds of formula (I) may be produced by process step (iii) an amine exchange reaction followed by cleavage of the protecting group under acidic or basic conditions, or with a nucleophile.

An alternative route is described in scheme 2:

Scheme 2

(I)

Compounds of formula (VI) may be made by reacting compound of formula (V) with suitable amine protecting group under the conditions of process step (i). Compounds of formula (VII) may be synthesised by steps consisting of the reduction and hydrolysis (in either order) of compounds of formula (VI). Compounds of formula (I) may be made by reacting compounds of formula (VII) under the conditions of process (v)—a reductive amination followed by removal of the protecting group. Suitable conditions are described under 'General Procedure A' in the experimental.

Compounds of formula (Ia) may also be synthesised as described in Scheme 3.

Scheme 3

Compounds of formula (VIII) in which the PG is acid labile are treated under acidic conditions of process step (vi) to remove the acid labile protecting group and form acid addition salt of (I), described as (Ia)

The invention also provides novel therapies for the treatment of disease.

Without being bound by theory, it appears the compounds of the present invention operate via a new drug pathway. They exploit an enzyme complex made of two proteins TGT (tRNA guanine transglycosylase) also known as queuine tRNA-ribosyltransferase 1, and Qv1 (queuine tRNA transglycosylase domain containing 1). The effect is to increase the relative populations of Treg cells and/or decrease populations of Teff cells. Treg cells are a part of the immune system that are intricately involved in the determination of self from non-self proteins i.e. protecting proteins of the self being attacked by the immune system (which is the cause of many autoimmune diseases). Further data to demonstrate the efficacy of the compounds is provided in the experimental section.

The transfer RNA (tRNA) of rapidly proliferating cells is deficient (hypomodified) in queuine modification; examples include foetal liver, multiple tumour types and regenerating adult liver. By contrast, the tRNA of adult, fully differentiated cells contains high levels of queuine, which cannot be displaced once incorporated.

It could be expected that the tRNA of rapidly expanding immune cells (as occurs in an autoimmune response) are likewise deficient in the queuine modification. Incorporation of novel Queuine Insertase substrates selectively into the queuine-deficient tRNA of immune cells could disrupt proliferation and cytokine production thereby modulating the immune response.

The present invention provides new medicaments for the treatment of autoimmune diseases, particularly multiple sclerosis.

This invention also relates to compounds of Formula (I)

(I)

Wherein:
$R^1$ is selected from H and $CH_3$
$R^2$ is selected from H, $C_4H_9$ alkyl, $C_6H_{13}$ alkyl, (1R,2S, 5S)-5-methylcyclopent-3-ene-1,2-diol and $C_3H_6$-phenyl, said phenyl optionally substituted by OH or $OCH_3$, X is O or S
Y is C, N or S.
and pharmaceutically acceptable salts and solvates thereof, for use as a medicament.

In a preferred embodiment
$R^1$ is selected from H and $CH_3$
$R^2$ is selected from H, $C_4H_9$ alkyl, $C_6H_{13}$ alkyl and $C_3H_6$-phenyl, said phenyl optionally substituted by OH or $OCH_3$,
X is O or S
Y is C, N or S.

The invention also provides for compounds of formula (I) for use in the treatment of autoimmune conditions such as rheumatoid arthritis, ulcerative colitis, psoriasis, diabetes and inflammatory bowel disease, including crohn's disease; and as agents to suppress transplant rejection.

This invention also relates to compounds of formula (I) as described above for use in the treatment of multiple sclerosis.

The invention also relates to a method of treating multiple sclerosis in a mammal, particularly a human, comprising administering to said mammal an amount of a compound of formula (I) as defined above, or a pharmaceutically acceptable salt or solvate thereof.

The term 'treatment' is intended to include curing, reversing, alleviating, palliative and prophylactic treatment of the condition.

The invention further relates to molecules of the invention in combination with other suitable agents, for use in the treatment multiple sclerosis.

Patients suffering from multiple sclerosis are commonly co-administered additional therapeutic agents. For patients suffering a severe attack, intravenous corticosteroids, such as methylprednisolone or techniques such as or plasmapheresis may be coadministered with any treatment.

The effects of nerve cell damage caused by multiple sclerosis result in diverse forms of damage to the patient. Nerve damage can lead to pain, difficulty with control of bladder and many other issues. For this reason, additional medicaments are often prescribed patients with multiple sclerosis to help treat the effects of MS damage. Suitable co-administrants would include:
For Bladder problems
botulinum toxin (Botox)
desmopressin (Desmospray, Desmotabs)
oxybutynin (Ditropan, Lyrinel)
tolterodine (Detrusitol)
For Depression
amitriptyline (Triptafen)
fluoxetine (Prozac)
imipramine (Tofranil)
paroxetine (Seroxat)
For Erectile dysfunction
alprostadil (Caverject, MUSE, Viridal Duo)
sildenafil citrate (Viagra)
tadalafil (Cialis)
vardenafil (Levitra)
For Fatigue
amantadine (Lysovir, Symmetrel)
modafinil (Provigil)
For Optic neuritis
steroids
For Pain
amitriptyline (Triptafen)
carbamazepine (Tegretol)
gabapentin (Neurontin)
ibuprofen
imipramine (Tofranil)
lamotrigine (Lamictal)
phenytoin (Epanutim)
pregabalin (Lyrica)
For Problems with walking
fampridine (Fampyra)
For Psuedobulbar affect
Nuedexta
For Spasticity and spasms
baclofen (Lioresal)
botulinum toxin (Botox)
carbamazepine (Tegretol)
clonazepam (Rivotril)
dantrolene (Dantrium)
diazepam (Valium)
gabapentin (Neurontin)
phenol
Tetrahydrocannabinol and cannabidiol (Sativex)
tizanidine (Zanaflex)
For Tremor
clonazepam (Rivotril)
thalamotomy
For Trigeminal neuralgia
carbamazepine (Tegretol)
gabapentin (Neurontin)
oxcarbazepine (Trileptal)
phenytoin (Epanutim)
pregabalin (Lyrica)
Other therapeutic agents are commonly administered to patients with MS. Other such medicaments are well known to physicians and others skilled in therapy.

Such agents may be administered sequentially, simultaneously or concomitantly.

The invention also relates to a pharmaceutical composition comprising a molecule of the present invention and a pharmaceutically acceptable diluent or carrier.

Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Compounds of formula (I) may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of formula (I) may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %. In one embodiment of the present invention, lubricants comprise from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO-A-00/35298.

Compounds of formula (I) may also be administered directly into the blood stream, into muscle, or into an internal organ. Such parenteral administration includes intravenous, intraarterial, intraperitoneal, intrathecal, intraventricular, intraurethral, intrasternal, intracranial, intramuscular and subcutaneous administration. Suitable devices for parenteral administration include needle (including microneedle) injectors, needle-free injectors and infusion techniques.

Compounds of the invention may also be administered topically to the skin or mucosa, that is, dermally or transdermally.

The compounds of formula (I) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3, 3-heptafluoropropane, or as nasal drops. For intranasal use, the powder may comprise a bioadhesive agent, for example, chitosan or cyclodextrin. For intranasal use, the powder may comprise a bioadhesive agent, for example, chitosan or cyclodextrin The pressurised container, pump, spray, atomizer, or nebuliser contains a solution or suspension of the compound of formula (I) comprising, for example, ethanol, aqueous ethanol, or a suitable alternative agent for dispersing, solubilising, or extending release of the compound, a propellant as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I) propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of formula (I) may also be administered directly to the eye or ear, typically in the form of drops of a micronised suspension or solution in isotonic, pH-adjusted, sterile saline.

Compounds of formula (I) may be combined with soluble macromolecular entities, such as cyclodextrin and suitable derivatives thereof or polyethylene glycol-containing polymers, in order to improve their solubility, dissolution rate, taste, bioavailability and/or stability when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in international patent publications WO-A-91/11172, WO-A-94/02518 and WO-A-98/55148.

Experimental

The synthesis of various molecules suitable for use in the present invention are described below.

All starting materials and reagents are commercially available and were obtained from Aldrich with exception of 2-amino-3H-pyrrolo[2,3-d]pyrimidin-4(7H)-one which was purchased from Fluorochem.

Preparation 1: 2-octanoylamino-pyrrolo[2,3-d]pyrimidin-4-one

A 50 cm$^3$ round-bottomed flask containing a stirring bar was charged with 2-amino-3H-pyrrolo[2,3-d]pyrimidin-4 (7H)-one (2.00 g, 13.33 mmol). The flask was fitted with a septum and placed under an Ar atmosphere. Freshly distilled pyridine (20.00 cm$^3$) was added via syringe and the resulting suspension cooled on ice. The solution was allowed to equilibrate at this temperature (ca. 5 min) and then octanoyl chloride (6.80 cm$^3$, 39.99 mmol) was added dropwise. The resulting suspension was heated at 85° C. for 30 min. After cooling to room temperature 6.5% ethanolic ammonia (60 cm$^3$) was added and the resulting suspension stirred at room temperature overnight. The precipitate of product was removed via vacuum filtration and washed with ethanol followed by diethyl ether to yield the desired product (2.56 g, 70%) pure as a yellow solid, m.p.>300° C. (decomposition). Procedure based on Akimoto et al. 1986 and Akimoto et al. 1988.

$\delta_H$ (400 MHz, DMSO-d$_6$): 0.86 (3H, t, J 5.1), 1.26 (8H, m), 1.58 (2H, app. quintet), 2.01 (1H, br s, NH), 2.43 (2H, t, J 5.1), 6.40 (1H, d, J 2.0), 7.01 (1H, d, J 2.0), 11.43 (1H, br s, NH), 11.67 (1H, br s, NH)

HRMS (m/z ESI$^-$): Found: 275.1517 ([M–H]$^-$ C$_{14}$H$_{19}$N$_4$O$_2$; Requires: 275.1508)

Preparation 2: 2-octanoylamino-5-((dibenzyl)amino) methyl)-pyrrolo[2,3-d]pyrimidin-4-one

A 50 cm$^3$ reaction vessel containing a stirring bar was charged with 2-octanoylamino-pyrrolo[2,3-d]pyrimidin-4-one (1.00 g, 3.60 mmol), dibenzylamine (2.00 cm$^3$, 10.80 mmol), formalin (349.00 μL, 12.60 mmol) and 80% aqueous acetic acid (36 cm³). The resulting suspension was heated at 60° C. for 20 h, cooled to room temperature, diluted with 0.5 M HCl (36 cm³) and stirred at room temperature for 30 min. The mixture was neutralised with conc. aq. ammonia (36 cm³) and extracted with chloroform (3×50 cm³). The organic extracts were combined, dried (MgSO₄) and evaporated to dryness. The crude residue was purified by column chromatography (9:1 dichloromethane-MeOH—7:3 dichloromethane-MeOH) to give the desired compound (1.45 g, 84%) as a yellow powder m.p.>300° C. (decomposition). Procedure based on Akimoto et al. 1986 and Akimoto et al. 1988.

$\delta_H$ (400 MHz, DMSO-d₆): 0.86 (3H, t, J 7.1), 1.25 (8H, m), 1.57 (2H, m) 2.42 (2H, t, J 7.1), 3.57 (4H, s), 3.76 (2H, s), 6.88 (1H, s), 7.23 (2H, t, J 7.3), 7.31 (4H, app. t), 7.41 (4H, d, 7.3), 11.34 (1H, s, NH), 11.57 (1H, s, NH), 11.68 (1H, s, NH)

HRMS (m/z ESI⁺): Found: 486.2863 ([M+H]⁺ $C_{29}H_{36}N_5O_2$; requires: 486.2869)

Example 1: 2-amino-5-(((3-phenylpropyl)amino)methyl)-3,7-dihydro-4H-pyrrolo[2,3-d]pyrimidin-4-one A large carousel tube containing a stirring bar was charged with 2-octanoylamino-5-((dibenzyl)amino)methyl)-pyrrolo[2,3-d]pyrimidin-4-one (100.0 mg, 0.21 mmol), 3-phenylpropylamine (146.00 µL, 1.03 mmol) and 1:1 THF-methanol (2.00 cm³). The suspension was degassed and the reaction vessel sealed. The suspension was heated at 75° C. for 24 h, cooled to room temperature and treated with 5 M KOH (146.00 µL) and stirred at room temperature for 65 h. The solution was concentrated in vacuo and the crude residue purified by column chromatography (9:0.9:0.1 dichloromethane-MeOH—NH₄OH). The resulting solid was washed with HPLC grade hexane followed by diethyl ether in order to remove trace impurities. This gave the desired compound (28 mg, 46%) as an orange powder, m.p.>300° C. (decomposition). Procedure based on Akimoto et al. 1986 and Akimoto et al. 1988.

$\delta_H$ (600 MHz, DMSO-d₆): 1.24 (1H, br s, NH), 1.66 (2H, app. quintet,), 1.91 (1H, s, NH), 2.44 (2H, t, J 6.9,), 2.57 (2H, t, J 6.9,), 3.59 (2H, s,), 6.15 (2H, br s,), 6.45 (1H, s,), 7.15 (1H, t, J 7.4,), 7.16 (3H, m), 7.25 (2H, app. t,), 10.70 (1H, br s)

$\delta_C$ (600 MHz, DMSO-d₆): 30.6, 32.9, 45.2, 47.5, 48.6, 79.2, 98.7 (q), 113.6 (q), 125.5, 128.2, 128.3, 142.3 (q), 152.2 (q), 160.5 (C=O)

$\nu_{max}$ (film)/cm⁻¹: 697, 748, 749, 1080, 1420, 1596, 2927

HRMS (m/z ESI⁺): Found: 298.1662 ([M+H]⁺ $C_{16}H_{20}N_6O$; Requires: 298.1668)

Preparation 3: 2-chloro-3-oxopropanenitrile

In a dry round bottomed flask under a positive pressure of argon, a suspension of NaOMe (7.14 g, 0.13 mol) in dry THF (90 mL) was cooled to −5° C. Methyl formate (9 mL, 0.15 mol) was added dropwise over 1 min by syringe and stirring was continued at −5° C. for 20 min. Then chloroacetonitrile (8.33 mL, 0.13 mol) was added dropwise via a dropping funnel over 45 min. The mixture turned from white to yellow and was stirred for a further 2 h at −5° C. at which point the reaction mixture was orange. The bath was removed and the reaction was allowed to warm up to room temperature. An aliquot of the reaction mixture was treated with a drop of concentrated HCl and analysed by TLC which indicated the presence of the desired product with an $R_f$=0.45, eluting with 100% EtOAc. The mixture was cooled to 0° C. and concentrated HCl (12 mL) was added dropwise during which time the mixture reaction became cherry-red. The resultant suspension was filtered through a pad of celite, and the celite was washed with EtOAc until the filtrate became colourless. The collected filtrates were concentrated at reduced pressure with the water bath at a temperature no higher than 40° C. to afford chloro(formypacetonitrile[1] as a black oil, in quantitative yield, which was used without further purification. Procedure based on Brooks 2012.

$\delta_H$ (400 MHz, CDCl₃) 9.38 (s, 1H).

$\delta_C$ NMR (400 MHz, DMSO-d₆) δ 168.2, 126.6, 67.8.

Preparation 4: 2-amino-4,7-dihydro-4-oxo-3H-pyrrolo[2,3-d]pyrimidine-5-carbonitrile 2,4-Diamino-6-hydroxypyrimidine (3.00 g, 24 mmol) was added to a solution of sodium acetate (6.4 g, 76 mmol) in millipore water (90 mL) and stirred at 50° C. for 1 hour. While still at 50° C. a solution of crude chloro(formyl) acetonitrile (3.00 g, 32 mmol) in mQ water (44 mL) was added dropwise with a dropping funnel, during which time the reaction turned beige and heating continued for 18 h at 50° C., after which time the reaction was heated to 100° C. for 3 h. The reaction mixture was allowed to cool to room temperature and the solid removed by filtration. The solid was suspended in EtOH and 5M aqueous KOH solution was added until the solid dissolved. Charcoal was added to the solution and the mixture stirred for 30 minutes before removal of the solid by filtration. The pH of the filtrate was adjusted to pH=6 with concentrated aqueous HCl solution during which time a precipitate formed and was collected by filtration. In order to remove the final traces of water from the solid it was dissolved in a mixture of toluene/methanol 1/1 and then concentrated at reduced pressure. The resultant solid was dried over $P_2O_5$ to afford the desired compound (1.68 g, 9.6 mmol, 40% yield) as beige solid. Procedure based on Brooks 2012.

$\delta_H$ (400 MHz, DMSO-$d_6$) δ 11.98 (br s, 1H) 10.74 (br s, 1H), 7.59 (s, 1H), 6.43 (s, 2H).

$\delta_C$ (100 MHz, DMSO-$d_6$) δ 158.0, 154.3, 152.1, 128.2, 116.4, 99.2, 86.0.

HRMS (m/z $C_7H_5N_5O$ [M–H]$^-$ Found 174.0415 Requires: 174.0416.

Preparation 5: 4,7-Dihydro-4-oxo-2-[(triphenylmethyl)amino]-3H-pyrrolo[2,3-d]pyrimidine-5-carbonitrile

In a dry round bottomed flask under an atmosphere of argon, trityl chloride (1.20 g, 4.28 mmol) was added to a solution of 2-amino-4,7-dihydro-4-oxo-3H-pyrrolo[2,3-d]pyrimidine-5-carbonitrile (0.50 g, 2.85 mmol) in dry pyridine (29 mL). The mixture reaction was heated at 90° C. for 48 h. The reaction mixture was concentrated under reduced pressure then absorbed on silica gel and purified by flash chromatography on silica gel eluting with dichloromethane/MeOH with a gradient starting at 2% of MeOH and rising to 10%. The desired compound was obtained as a brown solid (0.63 g, 1.5 mmol, 53% yield).

Procedure based on Ölgen 2008.

$\delta_H$ (400 MHz, DMSO-$d_6$) δ 11.80 (br s, 1H); 10.64 (br s, 1H), 7.56 (s, 1H), 7.41 (s, 1H), 7.29-7.28 (m, 12H), 7.23-7.17 (m, 3H), 5.73 (s, 1H).

HRMS (m/z ESI$^+$): $C_{26}H_{18}N_5O$ [M–H]$^+$ Found 416.1514 Requires: 416.1511.

Preparation 6: 4-oxo-2-(tritylamino)-4,7-dihydro-3H-pyrrolo[2,3-d]pyrimidine-5-carbaldehyde HMDS (6 mmol, 1.3 mL) was added to a mixture of 4,7-dihydro-4-oxo-2-[(triphenylmethyl)amino]-3H-pyrrolo[2,3-d]pyrimidine-5-carbonitrile (1.30 g, 3 mmol) with ammonium sulphate (397 mg, 0.3 mmol) in dry toluene (8 mL) in a round bottomed flask. A reflux condenser was fitted, and the flask was heated at reflux temperature overnight. The mixture was cooled to room temperature and concentrated under reduced pressure. Under a positive pressure of argon, the crude reaction mixture was solubilised in dry dichloromethane (8 mL) and cooled to −78° C. At this temperature, DiBAL-H (4.5 mL, 1 M in dichloromethane, 4.5 mmol) was added dropwise. After 2 hours, analysis by TLC (EtOAc 100%) indicated that some starting material remained. So, a further 2 mL DiBAL-H solution was added dropwise. After 1 hour, the reaction was complete and a mixture of $H_2O$/AcOH (9/1, 3.5 mL) was added at −78° C. The reaction mixture was allowed to warm to room temperature slowly. A mixture of EtOAc/$H_2O$ (1/1, 300 mL) was added to the reaction mixture and stirring continued at room temperature for 2 hours. The layers were separated and the organic layer was washed with brine and the aqueous layers were extracted with EtOAc. The combined organic fractions were dried over $MgSO_4$, filtered and concentrated at reduced pressure. The crude reaction product was filtered through a pad of silica gel eluting with EtOAc to afford a yellow solid (1.01 g, 2.38 mmol, 76%). Procedure based on Brooks 2010 and Brooks 2012.

$\delta_H$ (400 MHz, DMSO-$d_6$) δ 11.82 (s, 1H), 10.63 (s, 1H), 9.99 (s, 1H), 7.54 (s, 1H), 7.31-7.27 (m, 13H), 7.23-7.19 (m, 3H).

HRMS (m/z ESI$^-$): $C_{26}H_{18}N_4O_2$ [M–H]$^-$ Found 419.1508 Requires: 419.1508.

Preparation 7: 5-(((3-phenylpropyl)amino)methyl)-2-(tritylamino)-3,7-dihydro-4H-pyrrolo[2,3-d]pyrimidin-4-one

General procedure A: To a suspension of N-((4-oxo-2-(tritylamino)-4,7-dihydro-3H-pyrrolo[2,3-d]pyrimidin-5-yl)methyl)formamide (200.0 mg, 0.48 mmol) and sodium sulphate (5.0 mg) in methanol (5 cm$^3$) under an argon atmosphere was added 3-phenylpropylamine (74.00 µL, 0.52 mmol) and the resulting suspension stirred at room temperature for 2 h. Sodium borohydride (55.00 mg, 1.43 mmol) was then added and the reaction mixture stirred at room temperature for a further 1 h. Water (5 cm$^3$) was added and the resulting suspension stirred for 10 min before being extracted with dichloromethane (3×5 cm$^3$). The combined organic layers were dried ($MgSO_4$) and concentrated in vacuo to yield the crude product which was purified by flash chromatography (9:1 dichloromethane-MeOH) to yield the desired compound as a white solid (210 mg, 41.8%), m.p.>300° C. (decomposition). Procedure based on Brooks 2010 and Brooks 2012.

$^1$H (400 MHz, DMSO-$d_6$): 1.73 (2H, quintet, J 7.8), 2.56 (4H, m), 3.74 (1H, s), 6.42 (1H, s, H-6), 7.19 (20H, m), 7.45 (1H, bs, NH), 10.78 (1H, bs, NH)

$^{13}$C (400 MHz, DMSO-d$_6$): 31.7, 32.8, 45.4, 47.8, 70.4 (q), 99.7 (q), 114.9, 117.6 (q), 125.9, 126.0, 126.9, 128.0, 128.6, 129.0, 142.6 (q), 145.4 (q), 150.0 (q), 150.4 (q), 159.7 (C=O)

HRMS (m/z—ESI$^+$): Found: 540.2757 [M+H]$^+$ C$_{35}$H$_{34}$N$_5$O Requires: 540.2765) $v_{max}$/cm$^{-1}$: 1542, 1611, 1670, 2868, 2951

Example 2: N-((2-amino-4-oxo-4,7-dihydro-3H-pyrrolo[2,3-d]pyrimidin-5-yl)methyl)-3-phenylpropan-1-aminium chloride General procedure B: A 5 cm$^3$ reaction vessel containing a stirring bar was charged with 5-((3-phenylpropylamino) methyl)-2-(tritylamino)-3H-pyrrolo[2,3-d]pyrimidin-4(7H)-one (210.0 mg, 0.39 mmol) and 1.25 M methanolic HCl (3 cm$^3$). The resulting solution was stirred at room temperature for 16 h. The precipitated product was removed by vacuum filtration and washed with dichloromethane to yield the desired compound as a white powder (84 mg, 68%), m.p.>300° C. (decomposition). Procedure based on Brooks 2010 and Brooks 2012.

$\delta_H$ (600 MHz, DMSO-d$_6$): 1.90 (2H, app. quintet), 2.63 (2H, t, J 7.8), 2.90 (2H, m), 4.13 (2H, t, J 5.2), 6.57 (2H, bs), 6.80 (1H, d, J 2.3), 7.16 (3H, m), 7.26 (2H, t, J 7.0), 9.11 (2H, bs), 11.05 (1H, m, NH), 11.31 (1H, broad doublet, NH)

$\delta_C$ (125 MHz, DMSO-d$_6$): 27.6, 32.1, 42.9, 45.6, 48.9, 98.6, 108.7 (q), 117.9 (q), 126.4, 128.6, 128.7, 140.9 (q), 152.9 (q), 160.5 (C=O)

HRMS (m/z ESI$^+$): Found: 298.1662 (M$^+$ C$_{16}$H$_{20}$N$_5$O Requires: 298.1664)

$v_{max}$ (film)/cm$^{-1}$: 1456, 1625, 2443, 2713, 2756, 2873, 2933, 3184

Preparation 8 5-((3-butylamino)methyl)-2-(tritylamino)-3H-pyrrolo[2,3-d]pyrimidin-4(7H)-one Prepared as per general procedure A using N-((4-oxo-2-(tritylamino)-4,7-dihydro-3H-pyrrolo[2,3-d]pyrimidin-5-yl) methyl)formamide (200.00 mg, 0.48 mmol), n-butylamine (95.00 μL, 0.95 mmol) and NaBH$_4$ (55 mg, 1.43 mmol) to yield the desired product as a white powder (200 mg, 88%), m.p.>300° C. (decomposition).

$\delta_H$ (400 MHz, DMSO-d$_6$): 0.84 (3H, t, J 7.3), 1.30 (2H, app. sextet), 1.51 (2H, app. quintet), 2.82 (2H, t, J 7.3), 4.01 (2H, s), 6.62 (1H, s), 7.24 (15H, m), 7.57 (1H, bs), 11.07 (1H, bs)

$\delta_C$ (400 MHz, DMSO-d$_6$): 13.9, 19.6, 28.0, 42.9, 46.0, 70.6 (q), 99.4 (q), 108.9, 118.0 (q), 127.0, 128.1, 129.0, 145.2 (q), 150.5 (q), 150.6 (q), 160.3 (C=O)

$v_{max}$ (film)/cm$^{-1}$: 1545, 1613, 1672, 2870, 2956

HRMS (m/z ESI$^+$): Found: 478.2600 ([M+H]$^+$ C$_{30}$H$_{32}$N$_6$O; Requires: 478.2607)

Example 3 N-((2-amino-4-oxo-4,7-dihydro-3H-pyrrolo[2,3-d]pyrimidin-5-yl)methyl)butan-1-aminium chloride Prepared as per general procedure B using 5-((butylamino)methyl)-2-(tritylamino)-3H-pyrrolo[2,3-d]pyrimidin-4(7H)-one (108 mg, 0.39 mmol) and 1.25 M methanolic HCl (3 cm$^3$) to yield the desired product as a white powder (72 mg, 67%), m.p.>300° C. (decomposition).

$\delta_H$ (400 MHz, DMSO-d$_6$): 0.86 (3H, t, J 7.4), 1.31 (2H, app. sextet), 1.57 (2H, app. quintet), 2.90 (2H, m), 4.12 (2H, t, J 5.3), 6.49 (2H, bs), 6.81 (1H, s), 9.01 (2H, bs), 10.98 (2H, bs), 11.29 (1H, bs)

$\delta_C$ (400 MHz, DMSO-d$_6$): 18.7, 24.7, 32.7, 47.4, 50.6, 103.6 (q), 114.0, 123.2 (q), 153.3 (q), 157.6 (q), 164.7 (C=O)

HRMS (m/z ESI$^+$): Found: 236.1518 (M$^+$ C$_{11}$H$_{18}$N$_5$O Requires: 236.1511)

$v_{max}$ (film)/cm$^{-1}$: 1456, 1625, 1668, 2443, 2713, 2756, 2873, 2933, 3184

Preparation 9 5-((3-hexylamino)methyl)-2-(tritylamino)-3H-pyrrolo[2,3-d]pyrimidin-4(7H)-one Prepared as per general procedure A using N-((4-oxo-2-(tritylamino)-4,7-dihydro-3H-pyrrolo[2,3-d]pyrimidin-5-yl)

methyl)formamide (200.0 mg, 0.48 mmol), n-hexylamine (125.00 µL, 0.95 mmol) and sodium borohydride (55 mg, 1.43 mmol) to yield the desired product as a white powder (200 mg, 83.0%), m.p.>300° C. (decomposition).

$\delta_H$ (400 MHz, DMSO-$d_6$): 0.82 (3H, t, J 7.4), 1.20 (6H, m), 1.34 (2H, app. quintet), 2.40 (2H, t, J 7.4), 3.60 (2H, s), 6.30 (1H, s), 7.23 (15H, m), 7.37 (1H, bs), 10.62 (1H, bs)

$\delta_C$ (400 MHz, DMSO-$d_6$): 14.4, 22.5, 26.8, 31.6, 29.6, 45.2, 48.3, 70.4 (q), 99.7 (q), 115.2, 116.7 (q), 127.0, 128.1, 129.0, 145.4 (q), 150.1 (q), 150.5 (q), 159.7 (C=O)

$v_{max}$ (film)/cm$^{-1}$: 1552, 1648, 1734, 2856, 2928

HRMS (m/z ESI$^-$): Found: 504.2769 ([M–H]$^-$ $C_{32}H_{34}N_5O$; Requires: 504.2763)

Example 4 N-((2-amino-4-oxo-4,7-dihydro-3H-pyrrolo[2,3-d]pyrimidin-5-yl)methyl)hexan-1-aminium chloride Prepared as per general procedure B using 5-((hexylamino)methyl)-2-(tritylamino)-3H-pyrrolo[2,3-d]pyrimidin-4(7H)-one (190 mg, 0.39 mmol) and 1.25 M methanolic HCl (3 cm$^3$) to yield the desired product as a white powder (70 mg, 64.8%), m.p.>300° C.

$\delta_H$ (400 MHz, DMSO-$d_6$): 0.83 (3H, t, J 7.2), 1.25 (6H, m), 1.59 (2H, app. sextet, J 7.2), 2.87 (2H, m), 4.11 (2H, t, J 5.3), 6.71 (2H, bs), 6.84 (1H, d, J 3.6), 9.11 (2H, bs), 11.25 (1H, bs), 11.46 (1H, bs)

$\delta_C$ (400 MHz, DMSO-$d_6$): 14.3, 22.3, 25.8, 25.9, 31.1, 42.6, 46.1, 98.9 (q), 109.3 (q), 118.5, 148.1 (q), 152.8 (q), 159.8 (C=O)

$v_{max}$ (film)/cm$^{-1}$: 1578, 1625, 1669, 2429, 2712, 2861, 2930, 2957, 3266

HRMS (m/z ESI$^+$): Found: 264.1830 ([M+H]$^+$ $C_{13}H_{22}N_5O$ Requires: 264.1824)

H. Akimoto et al., J. Chem. Soc. Perkin Trans 1, 1998, 1627-1644.

H. Akimoto et al., J. Med. Chem., 1986, 29, 1749-1753.

S. Ölgen et al., Arch. Pharm. Chem. Life Sci., 2008, 341, 113-120.

A. F. Brooks et al., Tetrahedron Lett., 2010, 51, 4163-4165.

A. F. Brooks PhD Thesis "Synthesis of Tritium Labeled Queuine, PreQ1 and Related Azide Probes Toward Examining the Prevalence of Queuine" University of Michigan, 2012.

To assess the potential of these compounds in vivo, a chronic monophasic EAE disease in mice was induced before treatment with the new chemical entity (NCE). EAE Disease was induced in 8-10 week old female mice (C57BL/6) by subcutaneous (s.c.) injection of 200 µl emulsion containing 150 µg MOG$_{33-55}$ peptide (Genscript) in Complete Freund's Adjuvant (CFA; containing 5 mg/ml heat-inactivated *Mycobacterium tuberculosis*). On the same day, mice were administered 500 ng Pertussis Toxin (Kaketsuken, Japan) intraperitoneally (i.p.) and again two days later. Disease severity was recorded every 24 hours: 0-Normal; 1-flaccid tail; 2-imparied/wobbly gait; 3-complete hind limb weakness; 4-hind limb and forelimb paralysis; 5-moribund state/dead. Protocol is based on the Nature Protocols for Active induction of experimental allergic encephalomyelitis, which includes the scoring methodology:

Stromnes I M, Goverman J M (2006) Active induction of experimental allergic encephalomyelitis. Nat Protoc. 1(4): 1810-9.

Figure 1:
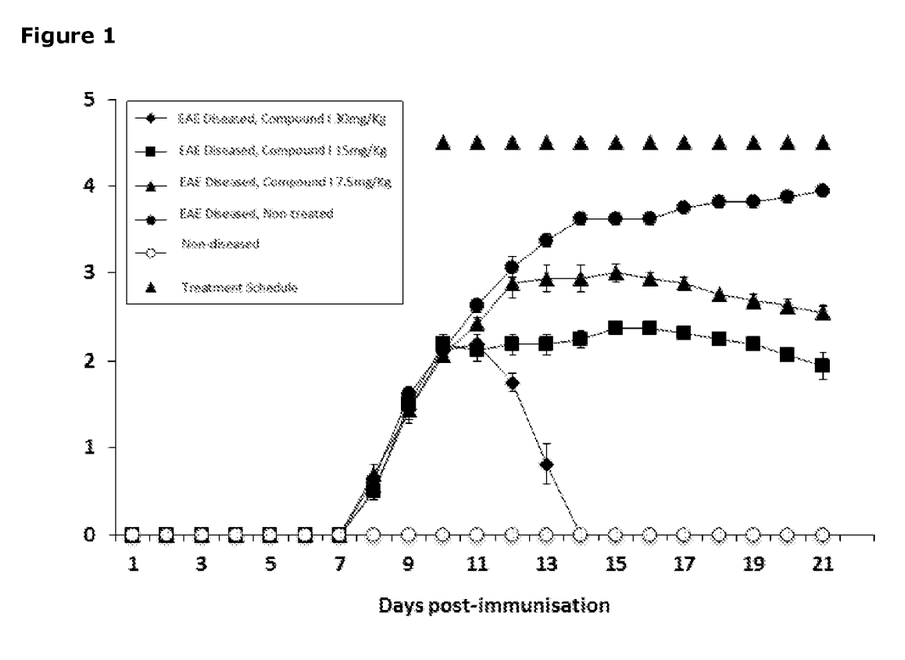
FIG. 1 shows results of in vivo testing with Compound I, measured by EAE score.

FIG. 1 shows the results of the in vivo testing for molecule N-((2-amino-4-oxo-4,7-dihydro-3H-pyrrolo[2,3-d]pyrimidin-5-yl)methyl)-3-phenylpropan-1-aminium chloride (Compound I). The EAE score relates to an assessment of disease progression with respect to issues like tail paralysis and limb paralysis, a higher score is a worse condition. A score of 1 indicates decreased tail tone, a score of 2 indicates hind leg weakness (paraparesis), a score of 3 indicates hind limb paralysis and/or incontinence. Note that the untreated animals have a continuous and progressive worsening of disease. In contrast, the animals treated with N-((2-amino-4-oxo-4,7-dihydro-3H-pyrrolo[2,3-d]pyrimidin-5-yl) methyl)-3-phenylpropan-1-aminium chloride (Compound I) exhibit rapid (within 24 hrs) reversal of symptoms at the highest dosage given (30 mg/kg, i.p.) and animals were scored as disease free after 4 daily treatments. At lower doses animals were slower to respond but in all cases disease progression was halted and reversed.

Figure 2:
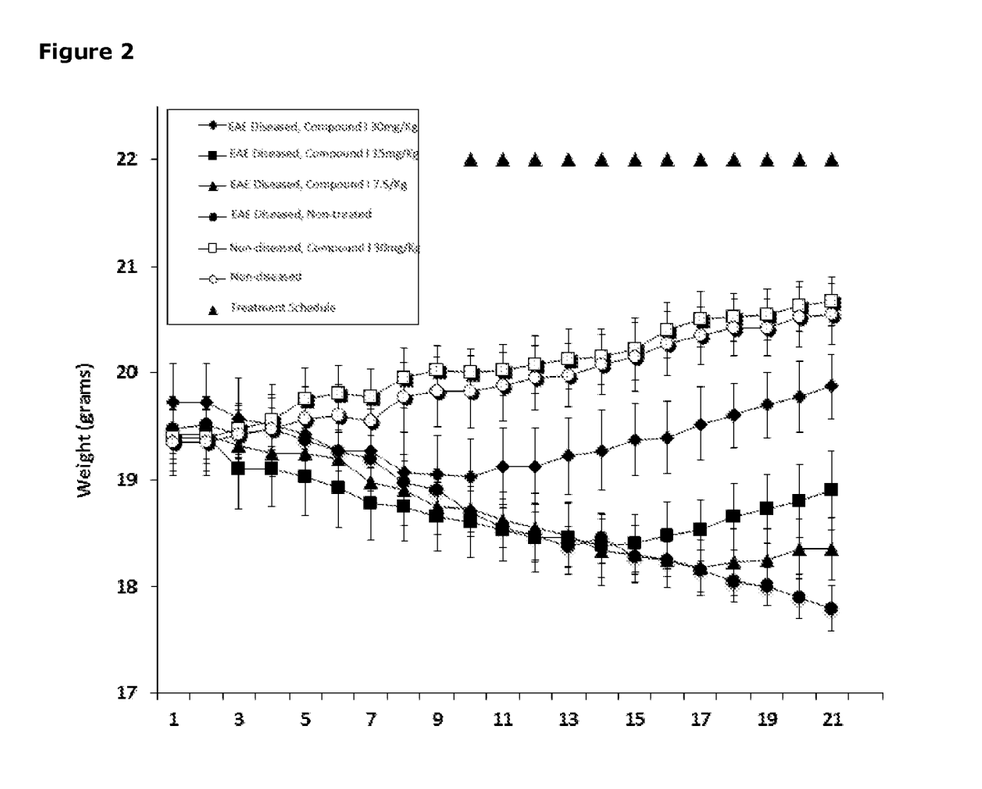
FIG. 2 shows results of in vivo testing with Compound I, measured by body weight.
Figure 3:
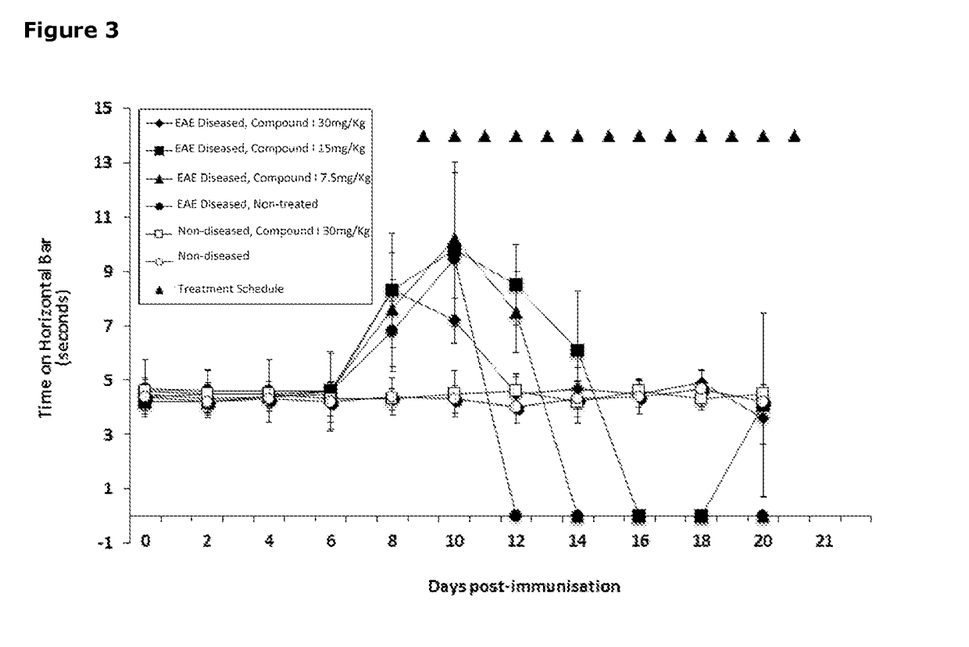
FIG. 3 shows results of in vivo testing with Compound I, measured by motor coordination and hind-limb strength.

FIG. 2 shows that in agreement with the observed disability scores, treated animals showed a dramatic return to normal weight gain, reaching a weight level 96.6% that of controls (19.9 grams versus 20.6 grams), at 21 days post inoculation (dpi). This contrasts with the sustained drop in body weight of non-treated EAE diseased animals to a level 86.4% that of controls at 21 dpi (17.8 grams versus 20.6 grams). Motor coordination and hind-limb strength were also evaluated by the ability of mice to cross a horizontal bar (FIG. 3). Non-diseased animals crossed the bar with an average time of 4.3±0.57 seconds. From 9 dpi, EAE mice showed a rapid deterioration in performance and were subsequently unable to maintain a grip on the apparatus. Strikingly, N-((2-amino-4-oxo-4,7-dihydro-3H-pyrrolo[2,3-d]pyrimidin-5-yl)methyl)-3-phenylpropan-1-aminium chloride (Compound I) treatment fully restored the performance of EAE diseased mice to control levels within 4 treatments.

The invention claimed is:

1. A method of treating a T-cell-mediated autoimmune disease in a mammal, the method comprising:
   administering to said mammal an amount of 2-amino-5-(((((1S,4S,5R)-4,5-dihydroxycyclopent-2-en-1-yl) amino)methyl)-3,7-dihydro-4H-pyrrolo [2,3-d]pyrimidin-4-one or a pharmaceutically acceptable salt thereof sufficient to treat said T-cell-mediated autoimmune disease,
   wherein treating is selected from one or more of: reversing progression of the T-cell-mediated autoimmune disease, alleviating the T-cell-mediated autoimmune disease, or palliatively treating the T-cell-mediated autoimmune disease.

2. The method of claim 1, wherein said T-cell-mediated autoimmune disease is selected from a group consisting of: rheumatoid arthritis, ulcerative colitis, psoriasis, transplant rejection, inflammatory bowel disease, Crohn's disease, and multiple sclerosis.

3. The method of claim 1, wherein said T-cell-mediated autoimmune disease is multiple sclerosis.

4. The method of claim 1, wherein said T-cell-mediated autoimmune disease is rheumatoid arthritis.

5. The method of claim 1, wherein said T-cell-mediated autoimmune disease is Crohn's disease.

6. The method of claim 1, wherein treating alleviates at least one symptom of the T-cell-mediated autoimmune disease.

7. The method of claim 1, wherein treating reverses progression of the T-cell-mediated autoimmune disease.

8. The method of claim 1, further comprising:
administering to said mammal at least one additional therapeutic agent.

9. A pharmaceutical composition comprising:
2-amino-5-((((1S,4S,5R)-4,5-dihydroxycyclopent-2-en1-yl)amino)methyl)-3,7-dihydro-4H-pyrrolo[2,3-d]pyrimidin-4-one or a pharmaceutically acceptable salt thereof in an amount effective for treating a T-cell-mediated autoimmune disorder; and
a pharmaceutically acceptable carrier or diluent,
wherein treating is selected from one or more of: reversing progression of the T-cell-mediated autoimmune disease, alleviating the T-cell-mediated autoimmune disease, or palliatively treating the T-cell-mediated autoimmune disease.

10. The pharmaceutical composition of claim 9, wherein said T-cell-mediated autoimmune disease is selected from a group consisting of: rheumatoid arthritis, ulcerative colitis, psoriasis, transplant rejection, inflammatory bowel disease, Crohn's disease, and multiple sclerosis.

11. The pharmaceutical composition of claim 9, wherein said T-cell-mediated autoimmune disease is multiple sclerosis.

12. The pharmaceutical composition of claim 9, wherein said T-cell-mediated autoimmune disease is rheumatoid arthritis.

13. The pharmaceutical composition of claim 9, wherein said T-cell-mediated autoimmune disease is Crohn's disease.

14. The pharmaceutical composition of claim 9, wherein treating alleviates at least one symptom of the T-cell-mediated autoimmune disease.

15. The pharmaceutical composition of claim 9, wherein treating reverses progression of the T-cell-mediated autoimmune disease.

16. The pharmaceutical composition of claim 9, further comprising:
at least one additional therapeutic agent.

* * * * *